United States Patent
Nagy et al.

(10) Patent No.: US 10,526,549 B2
(45) Date of Patent: Jan. 7, 2020

(54) BY-PRODUCT STREAM UPGRADING IN A PROPYLENE OXIDE/STYRENE COPRODUCTION PROCESS

(71) Applicant: Lyondell Chemical Technology, Houston, TX (US)

(72) Inventors: Sandor Nagy, Seabrook, TX (US); Dan D. Lindsey, Houston, TX (US); Barbara Kimmich, Houston, TX (US); Justin E. Turner, Conroe, TX (US); Nicholas Bruschi, Houston, TX (US); Ha H. Nguyen, Houston, TX (US); Pranit S. Metkar, Houston, TX (US); Anthony S. Dearth, Houston, TX (US)

(73) Assignee: Lyondell Chemical Technology, L.P., Houston, TX (US)

( * ) Notice: Subject to any disclaimer, the term of this patent is extended or adjusted under 35 U.S.C. 154(b) by 0 days.

(21) Appl. No.: 15/961,651

(22) Filed: Apr. 24, 2018

(65) Prior Publication Data

US 2018/0312764 A1    Nov. 1, 2018

Related U.S. Application Data

(60) Provisional application No. 62/492,619, filed on May 1, 2017.

(51) Int. Cl.

| | | |
|---|---|---|
| *C07C 5/56* | (2006.01) | |
| *C10G 45/08* | (2006.01) | |
| *C07C 15/46* | (2006.01) | |
| *C07D 303/04* | (2006.01) | |
| *B01J 27/051* | (2006.01) | |
| *C07D 301/08* | (2006.01) | |
| *C07C 1/22* | (2006.01) | |
| *C07D 301/19* | (2006.01) | |

(52) U.S. Cl.
CPC .......... *C10G 45/08* (2013.01); *B01J 27/0515* (2013.01); *C07C 1/22* (2013.01); *C07C 5/56* (2013.01); *C07C 15/46* (2013.01); *C07D 301/08* (2013.01); *C07D 303/04* (2013.01); *C07C 2523/28* (2013.01); *C07C 2523/755* (2013.01); *C07C 2523/883* (2013.01); *C07D 301/19* (2013.01); *C10G 2300/1096* (2013.01); *C10G 2300/202* (2013.01); *C10G 2400/30* (2013.01)

(58) Field of Classification Search
CPC ....... C07C 409/08; C07C 407/00; C07C 1/22; C07C 15/46; C07C 407/003; C07C 15/073; C07C 15/085; C07C 33/22
See application file for complete search history.

(56) References Cited

U.S. PATENT DOCUMENTS

| | | |
|---|---|---|
| 3,351,635 A | 11/1967 | Chong |
| 3,439,001 A | 4/1969 | Pell et al. |
| 3,944,627 A | 3/1976 | Schram et al. |
| 4,066,706 A | 1/1978 | Schmidt |
| 4,262,143 A | 4/1981 | Becker |
| 5,210,354 A * | 5/1993 | Dubner .................. C07C 15/46 585/435 |
| 5,276,235 A | 1/1994 | Dubner |
| 5,773,677 A | 6/1998 | Lansink-Rotgerink et al. |
| 6,080,894 A * | 6/2000 | Oyague .................... C07C 1/24 549/523 |
| 8,142,661 B2 | 3/2012 | Lindsey et al. |
| 8,815,084 B2 | 8/2014 | Escrig et al. |
| 2009/0143626 A1 * | 6/2009 | June ......................... C07C 1/22 568/840 |

FOREIGN PATENT DOCUMENTS

WO    2009021866 A1    2/2009

OTHER PUBLICATIONS

J.M. Bonnier et al., Unique Bimetallic Nickel-Chromium and Nickel-Molybdenum Catalysts for Hydrogenation in the Liquid Phase, Applied Catalysis, vol. 53, No. 2-3, Sep. 1, 1989, pp. 217-231, XP055494300.
Iwak et al., Hydrogenolysis of a-Methylbenzyl Alcohol over Bifunctional Catalysts, Applied Catalysis A: General 238 (2003), pp. 141-148.
The International Search Report and Written Opinion for PCT/US2018/029195 dated Jul. 31, 2018.

* cited by examiner

*Primary Examiner* — Sharon Pregler (57) ABSTRACT

The present disclosure relates to a method including subjecting an organic stream comprising at least one oxygenate to hydrotreatment, whereby a hydrotreatment product comprising ethylbenzene is produced, wherein the organic stream is a product of a process for the production of propylene oxide; and separating an ethylbenzene product stream from the hydrotreatment product, to yield a residual stream.

19 Claims, 4 Drawing Sheets

BY-PRODUCT STREAM UPGRADING IN A PROPYLENE OXIDE/STYRENE COPRODUCTION PROCESS

CROSS-REFERENCE TO RELATED APPLICATIONS

This application claims the benefit of priority to U.S. Provisional Application No. 62/492,619 filed on May 1, 2017, which is incorporated here by reference in its entirety.

FIELD OF THE INVENTION

This disclosure relates to by-product stream upgrading; more specifically, this disclosure relates to systems and methods for upgrading organic, oxygenate-containing streams obtained during propylene oxide production; still more specifically, this disclosure relates to systems and methods for treating, via hydrotreatment, oxygenate-containing process streams, formed in the production of propylene oxide or the co-production of propylene oxide and styrene monomer.

BACKGROUND OF THE INVENTION

The co-production of propylene oxide and styrene monomer, also referred to as the 'POSM' process, involves the oxidation of ethylbenzene to form ethylbenzene hydroperoxide, followed by the catalytic reaction of the hydroperoxide with propylene to form propylene oxide (PO) and 1-phenyl ethanol, and the dehydration of the 1-phenyl ethanol to produce styrene monomer. In the POSM process, various distillation steps are employed in order to separate unreacted reagents, as well as various product streams, and one or more washing steps may be employed in order to purify various streams. In the POSM process, and other such processes directed to the production of propylene oxide or other chemicals, a large volume of by-product streams comprising oxygenate(s) are generated. Without further treatment, these by-product stream(s) are a low value product stream that may be useful as a low grade fuel.

Accordingly, an ongoing need exists for systems and methods for upgrading low value organic, oxygenate-containing stream(s) produced in a variety of processes, such as, without limitation, PO or POSM production processes.

SUMMARY OF THE INVENTION

Herein disclosed is a method comprising: (a) subjecting an organic stream comprising at least one oxygenate to hydrotreatment, whereby a hydrotreatment product comprising ethylbenzene is produced, wherein the organic stream is a product of a process for the production of propylene oxide; and (b) separating an ethylbenzene product stream from the hydrotreatment product, to yield a residual stream.

Also disclosed herein is a method comprising: (a) providing a contaminated organic stream comprising at least one oxygenate and sodium contamination, wherein the organic stream is a product of a process for the production of propylene oxide; (b) reducing the level of sodium in the contaminated organic stream, to provide a pretreated organic stream; (c) subjecting the pretreated organic stream to hydrotreatment whereby a hydrotreatment product comprising ethylbenzene is produced; and (d) separating an ethylbenzene product stream from the hydrotreatment product, to provide a residual stream.

Also disclosed herein is a method comprising: (a) subjecting an organic stream comprising at least one oxygenate to hydrotreatment, whereby a hydrotreatment product comprising ethylbenzene is produced, wherein the organic stream is a product of a process for the co-production of propylene oxide and styrene monomer; (b) separating an ethylbenzene product stream from the hydrotreatment product, to yield a residual stream; and (c) reusing the separated ethylbenzene product as a feed in the process for the co-production of propylene oxide and styrene monomer.

While multiple embodiments are disclosed, still other embodiments will become apparent to those skilled in the art from the following detailed description. As will be apparent, certain embodiments, as disclosed herein, are capable of modifications in various aspects without departing from the spirit and scope of the claims as presented herein. Accordingly, the detailed description hereinbelow is to be regarded as illustrative in nature and not restrictive.

BRIEF DESCRIPTION OF THE DRAWINGS

The following figures illustrate embodiments of the subject matter disclosed herein. The claimed subject matter may be understood by reference to the following description taken in conjunction with the accompanying figures, in which like reference numerals identify like elements, and in which:

DETAILED DESCRIPTION OF THE INVENTION

Herein disclosed are systems and methods for upgrading organic oxygenate-containing streams, such as those generated in a propylene oxide production process. In embodiments, the organic streams are by-product streams generated in a POSM process. As noted hereinabove, large volumes of by-product streams which may be contaminated by ash (primarily sodium salts), and useful primarily as a low quality fuel, are produced during processes, such as the POSM process. The organic stream comprising oxygenate(s) may comprise a viscous/heavy residue generated in a POSM process.

Furthermore, although description of the herein-disclosed method and system are provided with reference to upgrading of a PO or POSM by-product stream, the herein-disclosed system and method may also be utilizable for upgrading of organic streams produced in other processes. Such organic streams produced in other processes include aromatic organic streams comprising oxygenates that can be converted into ethylbenzene via hydrodeoxygenation. As the organic stream may comprise a by-product from a PO or POSM process, and may be referred to herein as such, the organic stream is not intended to be limited to heavy residue or by-product from PO or POSM, but can be any organic stream comprising oxygenates which can be converted to product, such as ethylbenzene (EB), via hydrotreatment.

Herein disclosed are a system and method for upgrading an organic stream comprising oxygenate(s) that can be converted into ethylbenzene via hydrotreatment. Such an organic stream may be a by-product stream produced during the production of PO or the co-production of propylene oxide and styrene monomer.

Hydrotreatment

A system according to this disclosure comprises hydrotreatment unit operable to convert at least one oxygenate in the organic stream into ethylbenzene via hydrotreatment (including hydrodeoxygenation and/or hydrocracking), and a separation system or distillation apparatus operable to separate a light product comprising ethylbenzene from a heavy product residual stream. The hydrotreatment apparatus may also be referred to herein as a hydrodeoxygenation or hydrotreatment apparatus or a hydrodeoxygenation unit; although sometimes referred to as HDO or hydrodeoxygenation process (e.g., occurring in a hydrodeoxygenation unit or apparatus), it should be understood that hydrocracking may also be occurring. The system may further comprise organic stream production apparatus (also referred to herein as an 'organic stream production unit') operable to produce the organic stream, and pretreatment apparatus (also referred to herein as a 'pretreatment unit') operable to prepare the organic stream for hydrotreatment.

Figure 1A:
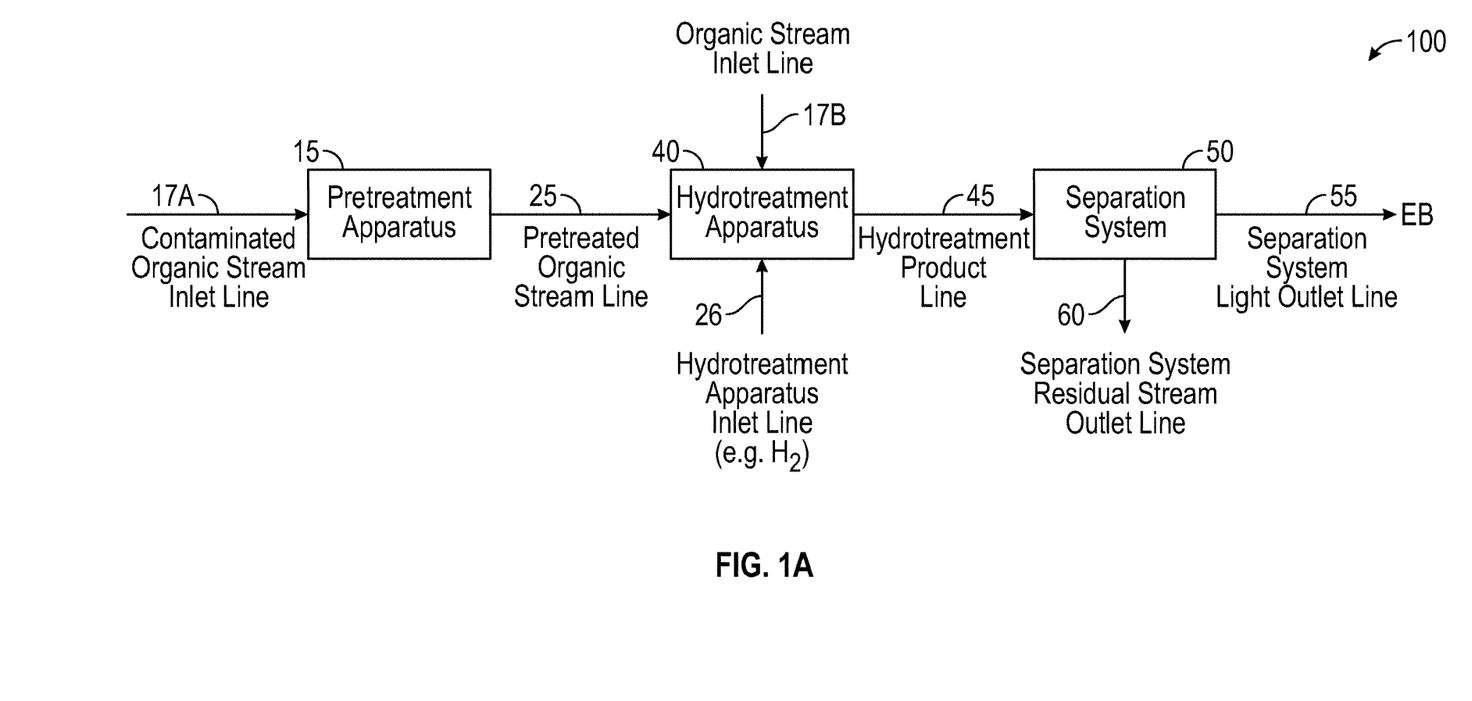
FIG. 1A is a schematic of a system for upgrading an organic stream according to an embodiment of this disclosure.

A system and method for upgrading such an organic stream will now be described with reference to FIG. 1A, which is a schematic of a system 100 for upgrading an organic stream according to an embodiment of this disclosure. System 100 of FIG. 1A comprises hydrotreatment unit 40, separation system or distillation apparatus 50, and pretreatment apparatus 15.

According to embodiments of this disclosure, an organic stream comprising at least one oxygenate is subjected to hydrotreatment (e.g., selective hydrodeoxygenation (HDO) and/or hydrocracking) in the hydrotreatment unit, whereby a hydrotreatment product comprising ethylbenzene is produced. For example, an organic stream can be introduced directly into hydrotreatment unit 40 via organic stream inlet line 17B; contaminated organic stream can be introduced via contaminated organic stream inlet line 17A into pretreatment apparatus 15, wherein it is treated for the removal of contaminant as described further hereinbelow, and a pretreated organic stream introduced into hydrotreatment unit 40 via pretreated organic stream line 25. Within hydrotreatment unit 40, the organic feed is converted into a hydrotreatment product comprising ethylbenzene, which may be removed from hydrotreatment unit 40 via hydrotreatment product line 45.

In embodiments, hydrotreatment is carried out in the presence of a heterogeneous hydrotreatment catalyst comprising molybdenum. In embodiments, the hydrotreatment catalyst further comprises nickel, cobalt, or a combination thereof. In embodiments, the hydrotreatment catalyst is a sulfided catalyst. In embodiments, the hydrotreatment catalyst comprises NiMo, CoMo, or a combination thereof. In embodiments, the hydrotreatment catalyst is not a copper-based catalyst. The hydrotreatment catalyst may be any commercially available NiMo or NiCo type catalysts, for example, CRI KL8233 or KL8234 KataLeuna catalyst available from Criterion Catalysts and Technologies of Shell Global Solutions, The Netherlands; bifunctional catalysts as described in Applied Catalysis A: General 238 (2003) 141-148; hydrogenolysis catalyst as described in U.S. Pat. No. 5,773,677; or another hydrotreatment catalyst employed by those of skill in the art.

In embodiments, the catalyst exhibits low selectivity to one or more byproducts and/or low ring hydrogenation of aromatics. For example, in embodiments, the hydrotreatment provides a hydrotreatment product comprising less than or equal to 0.2, 0.5, 1, 3, 5, 10, 15, or 20 weight percent ethylcyclohexane byproduct. The hydrotreatment catalyst may promote hydrogenolysis of oxygenates to EB, with little hydrogenation thereof to ethylcyclohexane.

One or more lines 26 may be utilized to introduce other components into hydrotreatment unit 40, or such component(s) may be combined with the organic stream to be hydrotreated prior to introduction thereof into hydrotreatment unit 40. For example, hydrogen may be introduced into hydrotreatment unit 40 via a line 26. Hydrogen may be introduced at a level to complete the process while avoiding a significant molar excess to avoid excessive recycling of the gas streams. In embodiments, hydrogen is combined with the liquid organic stream comprising oxygenate to be hydrotreated at a molar ratio to hydrotreatable components in the range of from about 2 to about 20, from about 3 to about 15, or from bout 4 to about 10. In embodiments, the hydrotreatment/hydrodeoxygenation may be performed continuously.

In some embodiments, the system comprises more than one hydrotreater, hydrotreatment reactor, or hydrotreatment step in series. In embodiments, the hydrotreatment unit comprises more than one hydrotreater or hydrotreatment reactor or hydrotreatment step in parallel. In embodiments, subjecting the organic stream comprising at least one oxygenate to hydrotreatment comprises introducing the organic stream to more than one hydrotreatment reactor in series, or introducing the organic stream to more than one hydrotreatment reactor in parallel. In embodiments, the hydrotreatment is operated at a reduced extent of feed conversion and the hydrotreatment product is recycled to the hydrotreatment unit, and/or a diluent as described hereinbelow is employed. Such methods may be utilized to control the temperature of the exothermic hydrotreatment. In embodiments, therefore, at least a portion of the hydrotreatment product is subjected to further hydrotreatment. In embodiments, a method of this disclosure comprises controlling the exothermicity of the hydrotreatment by operating the hydrotreatment at a reduced extent of reaction and recycling the hydrotreatment product to the hydrotreatment unit, adjusting the amount of a diluent combined with the organic stream, operating a plurality of hydrotreatment reactors in series, or a combination thereof. In embodiments, hydrotreatment is carried out adiabatically.

In embodiments, as noted above, the hydrotreatment is carried out in the presence of a diluent. As hydrodeoxygenation is exothermic, the use of a diluent may help control the temperature of the hydrotreatment. In embodiments, the diluent comprises ethylbenzene, which may be introduced into hydrotreatment unit 40 via a line 26, may be introduced into hydrotreatment unit 40 along with the organic stream 17B, and/or may be introduced during the pretreatment, for example introduced into contaminated (e.g., sodium-containing) organic stream inlet line 17A. The diluent may be introduced into hydrotreatment unit 40 along with the organic stream to be treated via organic line 17B, pretreated organic stream line 25 (described further hereinbelow), or both. In embodiments, the organic stream to be hydrotreated is combined (within and/or upstream of hydrotreatment unit 40) with a diluent at a mass ratio of organic stream to diluent that is in the range of from 1:0.1 to 1:10, from 1:0.5 to 1:5 from 1:1 to 1:3, or equal to 1:1.5, 1:2, or 1:2.5.

As described further hereinbelow with reference to the embodiment of FIG. 2, at least a portion of the heavies in separation system residual stream outlet line 60 separated from a light or ethylbenzene product stream in separation system 50 may be recycled to hydrotreatment unit 40, and introduced thereto, for example, via a hydrotreatment unit inlet line 26, at least a portion of the hydrotreatment product in hydrotreatment product line 45 can be recycled to hydrotreatment unit 40 via a line 26, at least a portion of the ethylbenzene product in separation system light outlet (or 'EB outlet') line 55 can be recycled to hydrotreatment unit 40 via a line 26, or a combination thereof.

The hydrotreatment unit may comprise a high temperature, high pressure hydrotreater. In embodiments, the hydrotreatment unit comprises a high temperature, high pressure hydrotreater comprising a fixed bed catalytic reactor. In embodiments, hydrotreatment is carried out at an inlet temperature in the range of from 150-300° C., from 180-280° C., or from 200-250° C. In embodiments, the hydrotreatment is carried out at an outlet temperature of greater than or equal to 300° C., 350° C., 400° C. or 450° C. Hydrotreatment may be carried out with an outlet temperature of greater than 300° C., 350° C., 400° C., or 450° C. after an initial catalyst break-in time. Higher temperatures may promote hydrocracking of components (e.g., diphenylbutanes) to EB. In embodiments, hydrotreatment is carried out at a pressure in the range of from 300-2000 psig, from 500-1500 psig, or from 800-1200 psig. In embodiments, hydrotreatment is carried out at a liquid hourly space velocity (LHSV) in the range of from 0.1-10 $h^{-1}$, from 0.5-5 $h^{-1}$, or from 0.8-2 $h^{-1}$.

In embodiments, the ethylbenzene recovery, defined as the weight percent of the organic stream introduced into hydrotreatment unit 40 that is converted to ethylbenzene, is greater than 20, 30, 40, 50 or 60 wt %. In embodiments, the conversion of at least one oxygenate to ethylbenzene is greater than or equal to 90, 93, or 95 wt %.

Separation

In embodiments, the method further comprises separating the hydrotreatment product into an ethylbenzene product stream and a residual stream. Separation may comprise distillation. In embodiments, separation comprises vacuum distillation. Vacuum distillation may be carried out at a pressure of less than or equal to 150 mm Hg, 100 mm Hg, or 50 mm Hg. In embodiments, distillation comprises subjecting the hydrotreatment product to distillation to separate the hydrotreatment product into a light stream comprising ethylbenzene, and a heavy stream comprising the residual stream. In embodiments, distillation comprises subjecting the hydrotreatment product to distillation to separate the hydrotreatment product into a light stream comprising primarily ethylbenzene, and a heavy stream comprising the residual stream. Thus, according to embodiments, the hydrotreatment product is introduced into separation system 50 via hydrotreatment product line 45, and a light or ethylbenzene product stream removed therefrom via ethylbenzene product outlet line 55, and a heavy or residual stream removed from separation system 50 via separation system residual stream outlet line 60. In embodiments, the light stream, the heavy stream, or both are subjected to further distillation to provide one or more further distilled streams. Thus, in embodiments, separation system 50 comprises one, two, or more distillation columns in series or in parallel. The heavy boiling compounds (also referred to as 'heavies') in separation system residual stream outlet line 60 may be put to use as a fuel, such as bunker fuel, heating oil, or further upgraded for use as a source of chemicals.

In embodiments, separation system 50 comprises a first distillation column operable to provide a light stream comprising ethylbenzene, from a heavy stream comprising the residual stream. In embodiments, the light stream comprising ethylbenzene is introduced into a second distillation column operable to separate a first stream comprising ethylbenzene from a second stream comprising ethylcyclohexane.

As discussed further hereinbelow with reference to the embodiment of FIG. 2, in embodiments, the light stream, the heavy stream, a further distilled stream, or a combination thereof is recycled to the hydrotreatment unit. In embodiments, at least a portion of the ethylbenzene product stream in separation system ethylbenzene outlet line 55, at least a portion of the residual stream in separation system residual stream outlet line 60, or both, are recycled to hydrotreatment unit 40 for further hydrotreatment.

Separating the ethylbenzene product stream from the hydrotreatment product (thereby yielding a residual stream in separation system residual stream line outlet line 60) may comprise recovering at least 20, 25, 30, 40, 50, or 60 weight percent of the ethylbenzene in the hydrotreatment product. The residual stream may comprise greater than or equal to 5, 10, 20, 50, or 70 weight percent diphenylbutane isomers. In embodiments, the residual stream comprises primarily diphenylbutane isomers. In embodiments, the residual stream comprises greater than or equal to 5, 10, 20, or 30 weight percent 2,3-diphenylbutane. In embodiments, separating the ethylbenzene product stream from the hydrotreatment product (thereby yielding a residual stream in separation system residual stream line outlet line 60) comprises recovering at least 50 weight percent of the ethylbenzene in the hydrotreatment product, and the residual stream is enriched in diphenylbutane isomers as major components. In embodiments, the residual stream comprises greater than or equal to 10, 11, 12, 13, or 14 weight percent of the meso form of 2,3-diphenylbutane. The method may further comprise crystallizing the meso form of the ethylbenzene dimer, 2,3-diphenylbutane, and separating it from the residual stream.

In embodiments, the residual stream in separation system residual stream outlet line 60 has a higher fuel value than the organic stream 17A/17B subjected to hydrotreatment in hydrotreatment unit 40. In embodiments, the residual stream has a higher caloric value than the organic stream. In embodiments, the residual stream has a density that is at least 3, 5, or 10 percent less than the density of the organic stream. In embodiments, the residual stream has a density of less than or equal to 0.97, 0.95, or 0.91 g/mL.

In embodiments, the residual stream comprises an oxygen content that is 20-100%, 30-90%, or 40-90% less than the oxygen content of the organic stream introduced into hydrotreatment unit 40. In embodiments, the residual stream has an oxygen content that is at least 70%, 80%, 90%, or 100% less than the oxygen content of the organic stream introduced into hydrotreatment unit 40. In embodiments, the residual stream has an oxygen content of less than or equal to 10, 5, 2, 1, or 0.1 wt %.

In embodiments, the residual stream has a viscosity of less than or equal to 20 cP, 10 cP, or 5 cP at 40° C.

Organic Stream to be Hydrotreated

As noted hereinabove, the organic stream comprising oxygenate(s) to be converted into ethylbenzene via hydrotreatment may be any organic stream comprising oxygenate(s) which can be converted into ethylbenzene via hydrotreatment. In embodiments, the organic stream comprises a product of a process for the production of propylene oxide (PO). In embodiments, the organic stream comprises a product of a process for the production of propylene oxide and styrene monomer (POSM).

A method according to this disclosure can further comprise producing the organic stream. For example, the organic stream to be hydrotreated may be produced in an organic stream generation process, such as via organic stream production unit 10 of the embodiment of FIG. 1B, which is a schematic of a system 100 for producing and upgrading an organic stream according to an embodiment of this disclosure. System 100 of FIG. 1B comprises hydrotreatment unit 40, separation system or distillation apparatus 50, organic stream production unit 10, and pretreatment unit 15, which in the embodiment of FIG. 1B comprises wash apparatus 20 and guard bed 30.

Figure 1B:
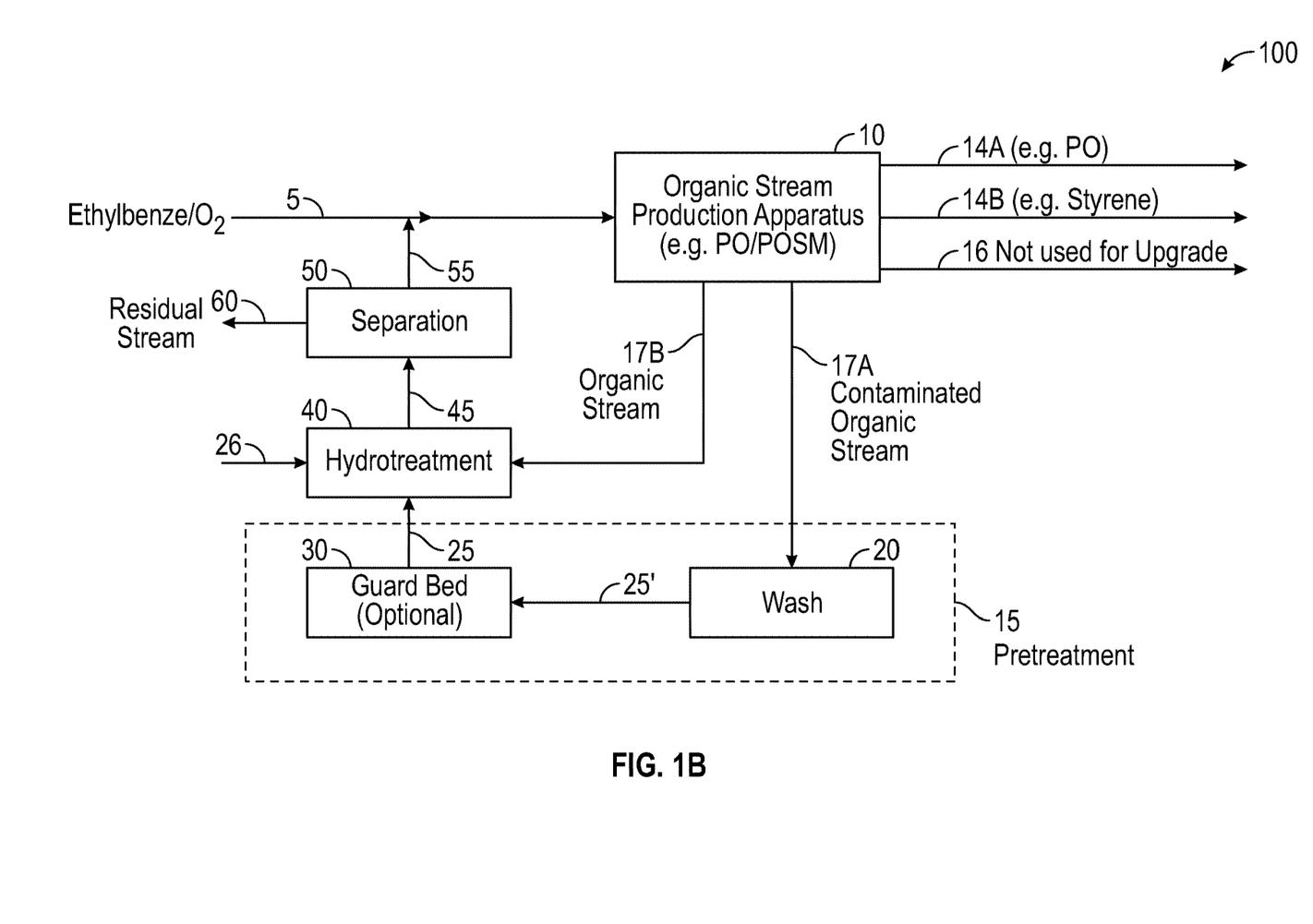
FIG. 1B is a schematic of a system for producing and upgrading an organic stream according to an embodiment of this disclosure.

In embodiments, organic stream production unit 10 comprises a PO production system. In embodiments, organic stream production unit 10 comprises a POSM production system. In embodiments, organic stream production unit 10 converts a feed comprising ethylbenzene and introduced thereto via ethylbenzene inlet line 5 and/or ethylbenzene product line 55 into one or more products 15. In embodiments, organic stream production system 10 comprises a PO production system. In such embodiments, a product outlet line 14A is configured for the removal of PO from PO production system 10. In embodiments, organic stream production unit 10 comprises a POSM production system. In such embodiments, a product outlet line 14A may be configured for removal of PO from POSM system 10, and a second product outlet line 14B may be configured for the removal of a styrene product therefrom. One or more lines 16 may be configured for the removal of waste not to be upgraded via hydrotreatment of this disclosure. Such material may be utilized in boilers or furnaces or sold as bunker fuel, for example.

In embodiments, the method further comprises generating, via a POSM process, a POSM by-product stream to be upgraded/hydrodeoxygenated according to the herein-disclosed system and method. Various POSM processes are commercialized, and an organic stream treated via the system and method of this disclosure can be produced via any such POSM process. For example, POSM processes and/or heavy residue streams therefrom are described in U.S. Pat. Nos. 3,351,635; 3,439,001; 4,066,706; 4,262,143; and 5,210,354, the disclosure of each of which is hereby incorporated herein by reference in its entirety for all purposes not contrary to this disclosure.

In embodiments of the POSM process via which a POSM organic stream to be hydrotreated is generated, ethylbenzene is reacted with molecular oxygen at elevated temperature to form ethylbenzene hydroperoxide. A small amount of alkali may be incorporated in the oxidation mixture in order to improve oxidation rate and selectivity. In embodiments, the ethylbenzene hydroperoxide is subsequently reacted with propylene (e.g., in the presence of an epoxidation catalyst, such as a molybdenum catalyst) to form propylene oxide and 1-phenyl ethanol (also referred to herein as methylbenzyl alcohol or MBA). The epoxidation reaction mixture may be caustic washed and subjected to a series of distillations in order to separate materials contained therein. In embodiments, the reaction mixture is distilled to separate unreacted propylene overhead from heavier components. The separated propylene may be recycled to the epoxidation step. In embodiments, the heavier components are further distilled, optionally after caustic wash, in a series of distillations to separate product propylene oxide, product 1-phenyl ethanol, and unreacted ethylbenzene, which can be recycled, optionally after a caustic wash. The 1-phenyl ethanol or MBA stream can be dehydrated to product styrene monomer, or subjected to hydrotreatment, as discussed further hereinbelow. In embodiments, a heavy organic low value product stream resulting from one or more step of such separations in a POSM process, or the like, is utilized as the organic stream to be hydrotreated and upgraded as described herein.

In embodiments, an organic heavy residue stream from a propylene oxide/styrene monomer process, subjected to hydrotreatment according to this disclosure, comprises primarily oxygenated aryl compounds, which may have, without limitation, molecular weights greater than or equal to 90 g/mol, 94 g/mol, 200 g/mol, 215 g/mol, or 225 g/mol. In embodiments, the heavy organic residue stream from the propylene oxide/styrene monomer process comprises oxygenated aryl compounds. In embodiments, the heavy organic residue stream from the propylene oxide/styrene monomer process comprises primarily oxygenated aryl compounds. In embodiments, the heavy organic residue stream from the propylene oxide/styrene monomer process comprises at least 20, 30, 40, or 50 weight percent oxygenated aryl compounds.

In embodiments, organic stream production unit 10 produces MBA and byproduct acetophenone (ACP). According to embodiments of this disclosure, rather than converting the ACP to MBA in a hydrogenation unit, and the MBA to styrene via dehydration, an ACP/MBA stream comprising ACP and MBA is hydrotreated as described herein to provide additional EB. In embodiments, the organic stream to be hydrotreated thus comprises an ACP/MBA stream from a POSM system. Utilization of the MBA and/or ACP as the organic stream may alter the styrene monomer to ethylbenzene (SM:EB) ratio provided in the POSM process. In embodiments, the production of SM may be reduced at constant PO production by converting a slipstream of MBA/ACP to EB as described herein.

In embodiments, organic stream production unit 10 comprises a wiped film evaporation (WFE) that produces a volatile overhead fraction. In embodiments, the organic stream comprising oxygenate to be converted to EB comprises a portion of such an overhead fraction. Such a WFE overhead may comprise a high level of 2-phenylethanol along with MBA and ACP.

In embodiments, the at least one oxygenate in the organic stream comprises MBA, 2-phenylethanol (phenylethyl alcohol or PEA), ethers, ACP, ethers of MBA and PEA, propylene oxide ring opening compounds, oligomers (e.g., oligomers of styrene, including dimers and trimers thereof), or a combination thereof. In embodiments, the ethers of MBA comprise 1-20 wt % of the oxygenate in the organic stream. In embodiments, the ethers of PEA comprise 1-20% wt % of the oxygenate in the organic stream. In embodiments, the PO ring opening compounds or isomers comprise 1-20 wt % of the oxygenate in the organic stream.

In embodiments, the organic stream is a POSM co-product stream that has not been treated to remove heavies therefrom. For example, in embodiments, the organic stream is a heavy residue that has not been subjected to flash distillation or the like to remove heavies therefrom. In embodiments, flash distillation is avoided, as it may generate distillation bottoms that are difficult to handle and dispose.

In embodiments, the organic stream comprising oxygenate to be converted into ethylbenzene also comprises a contaminant. The contaminant may be sodium, which may, for example, originate from caustic washes utilized in the POSM process. In embodiments, the contamination comprises greater than or equal to 97%, 98%, or 99% sodium salts. The contamination may further comprise minor amounts of other metals, such as, without limitation, Fe, Mg, Ca, and K. In embodiments, the contaminant comprises sodium, potassium, or both. In embodiments, the organic stream comprises greater than or equal to 0.01 wt % (100 ppm), 0.1 wt % (1,000 ppm), 0.25 wt % (2,500 ppm), 0.3 wt % (3,000 ppm), 0.4 wt % (4,000 ppm), 0.5 wt % (5,000 ppm), 0.75 wt % (7,500 ppm), 1.0 wt % (10,000 ppm), 2.5 wt % (25,000 ppm), or 5 wt % (50,000 ppm) sodium and/or potassium. In embodiments, the organic stream comprises from 0.01 wt % (100 ppm) to 5 wt % (50,000 ppm), from 0.01 wt % (100 ppm) to 2.5 wt % (25,000 ppm), or from 0.01 wt % (100 ppm) to 1 wt % (10,000 ppm) sodium and/or potassium. In embodiments, the organic stream comprising oxygenate to be converted into ethylbenzene comprises less than 500, 250, 100, 50, 10, or 1 ppm sodium and/or potassium, and is introduced directly into hydrotreatment unit 40, for example via organic stream inlet line 17B.

Pretreatment

In embodiments, the organic stream comprising the oxygenate to be converted into ethylbenzene is a sodium and/or potassium contaminated organic stream that is treated for removal of at least a portion of the contaminant to provide a pretreated organic stream, prior to subjecting the pretreated organic stream to hydrotreatment. In embodiments, the pretreated organic stream in pretreated organic stream line 25 comprises less than 500, 250, 100, 50, 10, or 1 ppm of sodium and/or potassium. Removing at least a portion of the contaminant prior to hydrotreatment can comprise subjecting the contaminated organic stream to an acid wash and subsequent neutralization to provide a pretreated organic stream; contacting the organic stream with water and carbon dioxide, whereby sodium is extracted from the organic stream, and separating an aqueous sodium-containing slurry phase from a pretreated organic stream comprising a reduced sodium content relative to the contaminated organic stream; passing the contaminated organic stream over a catalyst guard bed to provide the pretreated organic stream prior to hydrotreatment; or a combination thereof.

In embodiments, a contaminated organic stream is introduced via contaminated organic line 17A into pretreatment unit 15, wherein contaminant is removed to provide a pretreated organic stream in pretreated organic stream line 25. Pretreatment unit 15 may comprise a wash 20/220 as depicted in the embodiments of FIG. 1B and FIG. 2 (which is described further hereinbelow), a $CO_2$ treatment, as depicted in the embodiment of FIG. 3 (which is described further hereinbelow), and/or a guard bed, as depicted in the embodiments of FIGS. 1B and 3 (which is described further hereinbelow).

With reference to FIG. 1B, in embodiments, a contaminated organic stream is introduced via contaminated organic stream line 17A into wash apparatus 20 and/or guard bed 30 prior to introduction into hydrotreatment unit 40. In embodiments, a contaminated organic stream is introduced via one or more contaminated organic stream lines 17A into wash apparatus 20. Washed organic stream removed from wash apparatus 20 via washed or pretreated organic stream line 25' may be introduced directly into hydrotreatment unit 40, or may be introduced into a guard bed 30 operable to further reduce the level of contaminant therein. Alternatively, the contaminated organic stream in line 17A can be introduced directly into guard bed 30.

As discussed further with reference to FIG. 2 hereinbelow, make-up fresh ethylbenzene and/or recycled EB comprising a portion of the ethylbenzene in separation system ethylbenzene outlet line 55 may be introduced into pretreatment apparatus 15, and/or heavies from separation system 50 may be recycled to pretreatment apparatus 15.

The contaminated organic stream may be treated in pretreatment 15 to provide a pretreated organic stream comprising less than 500, 250, 100, 50, 10, or 1 ppm sodium and/or potassium, which may be introduced into hydrotreatment unit 40 via pretreated organic stream line 25 or line 25'. In embodiments, the feed to hydrotreatment unit 40 is close to neutral.

Guard Bed

As noted above, removing at least a portion of the contaminant prior to hydrotreatment can comprise passing the contaminated organic stream over a catalyst guard bed to provide the pretreated stream prior to hydrotreatment. In the embodiment of FIG. 1B, contaminated organic phase is washed in wash system 20, and the washed organic phase in pretreated organic stream line 25' is introduced into guard bed 30, wherein trace sodium is removed therefrom. A pretreated organic stream comprising reduced contaminant is introduced into hydrotreatment unit 40 via pretreated organic stream line 25. Guard bed 30 may comprise a solid material capable of efficiently retaining metal ions. Examples of these materials include, without limitation, ion exchangers such as zeolites, clays and ion resins in H-form.

Within guard bed 30, the organic stream can be subjected to one or more ion exchange 'polishing' steps to further reduce the sodium content thereof. Subjecting the organic stream to ion exchange, may comprise subjecting the organic stream to cation exchange. Ion exchange may be effected via any ion exchange used by those of skill in the art. For example, in embodiments, ion exchange is effected with an ion exchange resin comprising sulfonic acid groups. The ion exchange may be carried out utilizing an ion exchange media that is natural or synthetic. In embodiments, the ion exchange is effected with an ion exchange resin selected from the group consisting of polymer resins, zeolites, clays, and combinations thereof. For example, the acidic form of zeolites and/or layered materials, such as clays, may provide effective ion exchange media, in embodiments.

Wash

In embodiments, as noted hereinabove, removing at least a portion of the contaminant prior to hydrotreatment comprises subjecting the organic stream to an acid wash and subsequent neutralization to provide a pretreated organic stream. The organic stream may be water washed subsequent to acid wash, neutralization, or both. In embodiments, subjecting the organic stream to acid wash and subsequent neutralization to provide a pretreated organic stream is performed as described in U.S. Pat. Nos. 8,142,661, or 8,815,084, the disclosure of each of which is hereby incorporated herein in its entirety for purposes not contrary to this disclosure.

Wash apparatus, such as wash apparatus 20 of FIG. 1B, will now be further described hereinbelow with reference to the embodiment of FIG. 2, which is a schematic of a system for upgrading an organic stream according to an another embodiment of this disclosure. In the embodiment of FIG. 2, a system 200 for upgrading an organic stream according to an embodiment of this disclosure comprises wash apparatus 220 including acid wash unit 220A, water wash unit 220B, carbonate or bicarbonate wash (e.g., sodium, potassium and/or ammonium carbonate) or neutralization unit 220C, and water wash unit 220D. An organic stream comprising oxygenate to be converted into ethylbenzene (e.g., contaminated organic stream inlet line 17A of FIG. 1A) is introduced via contaminated organic stream inlet line 217A into acid wash unit 220A. Make-up fresh ethylbenzene may be introduced into acid wash unit 220A via make-up EB line 205, recycled EB (e.g., a portion of separation system light outlet line 55 of FIG. 1A) may be introduced into acid wash unit 220A via EB recycle line 255B, and/or recycled heavies (e.g., a portion of separation system residual stream outlet line 60 of FIG. 1A) may be introduced into acid wash unit 220A via separation system residual stream recycle line 2603.

Before and/or within acid wash unit 220A, the organic stream is contacted with an acid solution (in acid line 221A) to provide an acid-washed organic stream. Acid, such as, without limitation, sulfuric acid solution or hydrochloric acid solution, can be introduced via acid inlet line 221A into acid wash unit 220A.

Waste line 222A comprising at least a portion of the removed contaminant (e.g., sodium) is removed from acid wash unit 220A via waste line 222A. In embodiments, an acid washed organic stream is introduced via acid washed organic stream line 225A into a water wash unit 220B. The acid washed organic stream in line 225A may comprise less than 200, 100, 10 or 1 ppm sodium. In alternative embodiments, the acid washed organic stream is introduced directly into neutralization unit 220C. Water can be introduced into water wash unit 220B via water inlet line 221B. A water-washed organic stream can be introduced via water-washed organic stream line 225B into neutralization unit 220C, and waste water removed from water wash unit 220B via water wash outlet line 222B. Water in water wash outlet line 222B can be recycled and mixed with acid in acid line 221A and/or water in water inlet line 221B. The acid and water washed organic stream in line 225B may comprise less than 100, 10, or 1 ppm sodium.

Within neutralization unit 220C, the acid-washed organic stream is neutralized. Neutralization can comprise contacting the acid and/or water washed organic stream with a neutralization agent. The neutralization agent can comprise carbonate, crushed marble, or a combination thereof. The carbonate can comprise ammonium carbonate, sodium carbonate, or both. Neutralization agent can be introduced into neutralization unit 220C via neutralization agent inlet line 221C, or may be (e.g., marble) contained within unit 220C. Waste material may be removed from neutralization unit 220C via waste line 222C. Neutralized organic stream in neutralized organic stream line 225C may comprise less than 100, 10 or 1 ppm sodium.

In embodiments, the neutralized organic stream in line 225C is water washed. In embodiments, the neutralized organic stream is introduced via neutralization unit outlet line 225C into water wash unit 220D. Water is introduced into water wash unit 220D via water inlet line 221D, and removed therefrom via water wash outlet line 222D. Water in water wash outlet line 222D can be recycled and mixed with acid in acid line 221A and/or water in water inlet line 221B. Pretreated organic stream can be removed from water wash unit 220D via washed organic stream line 225D, which, like washed organic stream in washed organic stream line 25' of FIG. 1B can be fed directly into hydrotreatment unit 240 or via guard bed 230, which may be operable as described with reference to guard bed 30 of FIG. 1B. As noted hereinabove, the pretreated organic stream in line 225D can comprise less than 100, 10, or 1 ppm sodium, in embodiments.

The pretreated organic phase/stream in washed organic stream line 225D exiting wash apparatus 220 or pretreated organic stream line 225E exiting guard bed 230 is introduced into hydrotreatment reactor 240. Recycled hydrotreatment product can be introduced into hydrotreatment reactor 240 via hydrotreatment product recycle line 245A. Recycled heavies can be introduced into hydrotreatment reactor 240 via separation system residual stream recycle line 260B. Within hydrotreatment reactor 240, hydrodeoxygenation of oxygenate(s) in the organic stream proceeds via combination with hydrogen, introduced into hydrotreatment reactor 240 via hydrotreatment unit inlet line 226. Hydrotreatment may be carried out as described hereinabove with reference to hydrotreatment unit 40 of FIG. 1A. Hydrotreatment product is removed from hydrotreatment reactor or system 240 via hydrotreatment product line 245. A portion of the hydrotreatment product can be recycled to hydrotreatment reactor 240, via hydrotreatment product recycle line 245A. Such recycle may be utilized when hydrotreatment reactor 240 is operated at a lower extent of reaction, for example, to control temperature.

As noted above with reference to the embodiment of FIG. 1A, the ethylbenzene recovery, defined as the weight percent of the organic stream introduced into hydrotreatment system 240 that is converted to ethylbenzene, can be greater than 20, 30, 40, 50 or 60 wt %, in embodiments. In embodiments, the conversion of the at least one oxygenate to ethylbenzene is greater than or equal to 90, 93, or 95 wt %.

Hydrotreatment product can be introduced into separation system 250, which can comprise one or more distillation columns, via hydrotreatment product line 245. Separation system 250 can be operated as described hereinabove with reference to separation system 50 of the embodiment of FIG. 1A. Within separation system 250, a light stream comprising ethylbenzene can be separated from a heavy or residual stream. The light stream comprising ethylbenzene can be removed from separation system 250 via separation system light or EB outlet line 255, and the heavy or residual stream removed from separation system 250 via separation system residual stream outlet line 260. The light stream may comprise greater than 90, 95 or 97 percent EB. In embodiments, the light stream comprises primarily EB. Separating the ethylbenzene product stream from the hydrotreatment product may comprise recovering at least 20, 30, 40, 50, or 60 weight percent of the ethylbenzene in the hydrotreatment product of hydrotreatment product line 245.

The heavy or residual stream can be removed from separation system 250 via separation system residual stream outlet line 260. As noted above, the residual stream may comprise greater than or equal to 5, 10, 20, 50, or 70 weight percent diphenylbutane isomers. In embodiments, the heavy or residual stream comprises primarily diphenylbutanes. In embodiments, the residual stream comprises greater than or equal to 5, 10, 20, or 30 weight percent 2,3-diphenylbutane. The method may further comprise crystallizing the meso form of the 2,3-diphenylbutane, and separating it from the residual stream.

Figure 2:
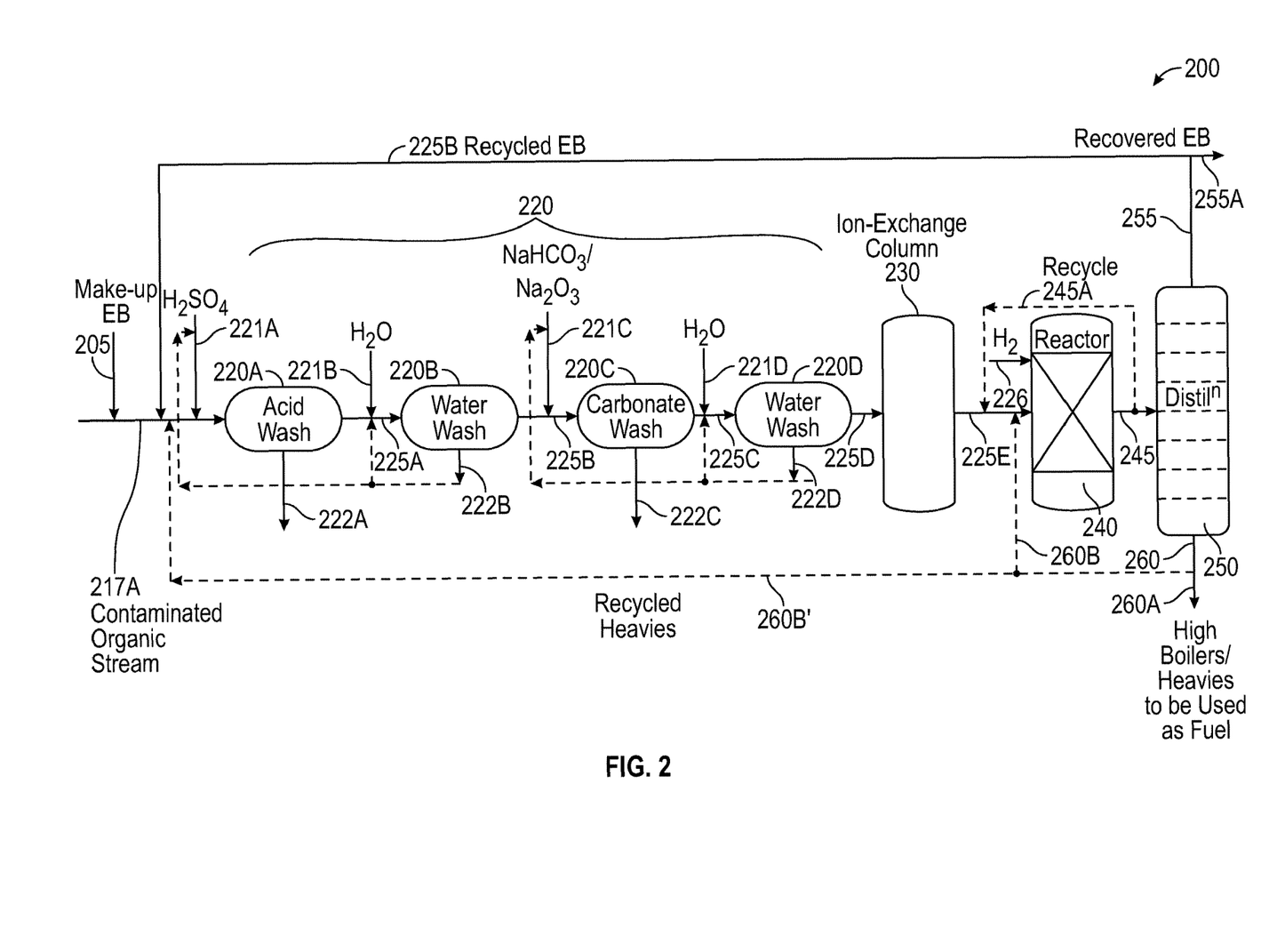
FIG. 2 is a schematic of a system for upgrading an organic stream according to an another embodiment of this disclosure.
Figure 3:
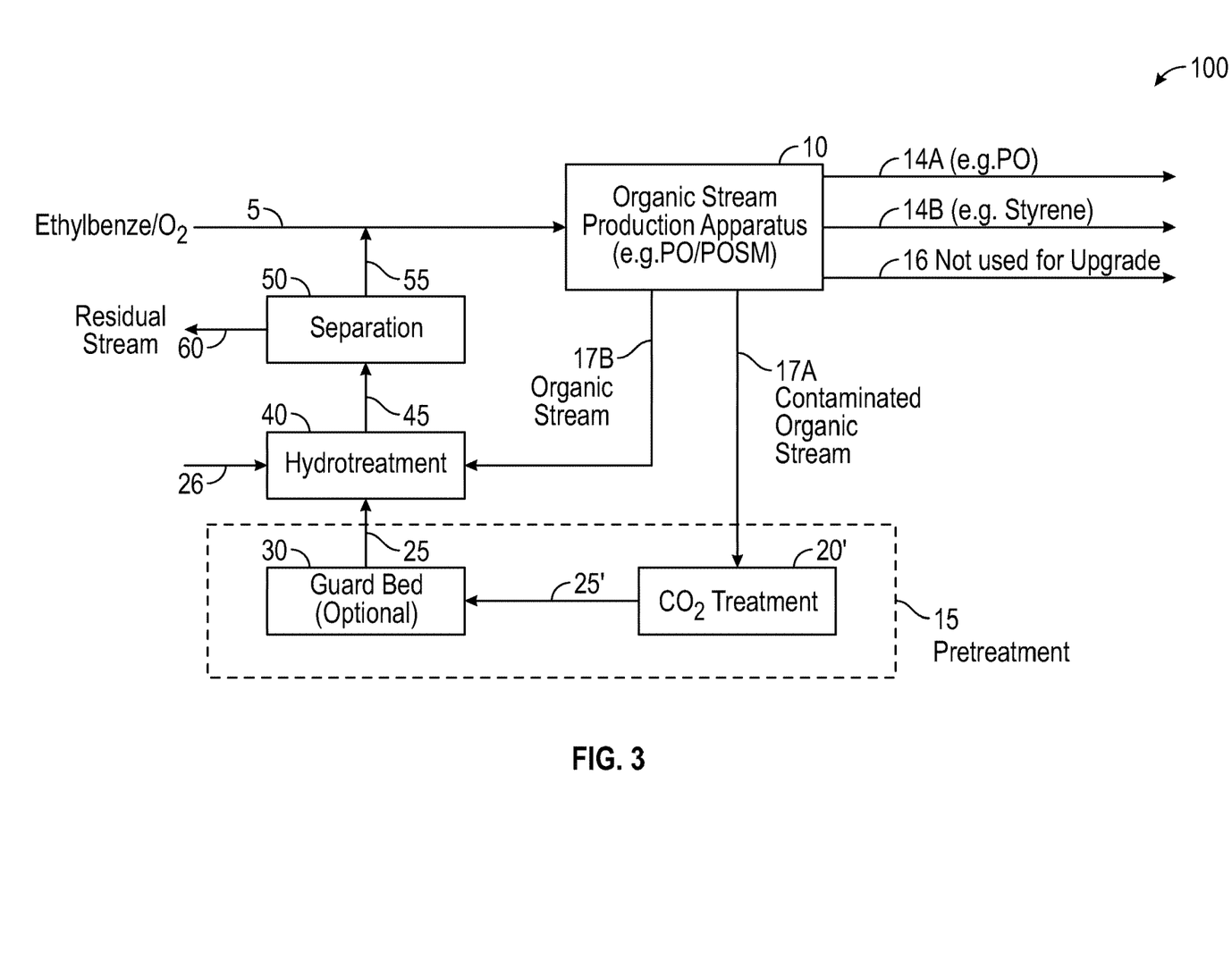
FIG. 3 is a schematic of a system for producing and upgrading an organic stream according to an embodiment of this disclosure.

At least a portion of the light stream can be reintroduced into hydrotreatment reactor or hydrotreatment system 240, for example via combination with contaminated organic stream in contaminated organic stream line 217A via recycle EB line 255B or via combination with pretreated organic stream in line 225D (not shown in the embodiment of FIG. 2). At least a portion of the heavy stream can be reintroduced into hydrotreatment reactor 240, for example via combination with contaminated organic stream in contaminated organic stream line 217A via separation system recycled residual stream line 260B' or via combination with pretreated organic stream line 225E via separation system recycled residual stream line 260B.

The unrecycled residual stream in separation system unrecycled residual stream line 260A can be utilized as bunker fuel, further treated for use as a fuel, or used as a chemical precursor as noted hereinabove with reference to line 60 of the embodiment of FIG. 1A. The recovered EB can be utilized in a downstream organic stream production apparatus, such as organic stream production unit 10 described hereinabove with reference to the embodiment of FIG. 1B. For example, the recovered EB in recovered EB line 255A can be utilized in a PO or POSM process/system. In embodiments, the recovered EB is introduced into an oxidizer of a POSM process configured for autooxidation of EB to form ethylbenzene hydroperoxide.

Carbon Dioxide Pretreatment

As noted hereinabove, in embodiments, pretreatment to remove at least a portion of the contaminant prior to hydrotreatment comprises carbon dioxide treatment. FIG. 3 is a schematic of a system for producing and upgrading an organic stream according to another embodiment of this disclosure. System 100 of FIG. 3 is consistent with system 100 of FIG. 1B, with pretreatment 15 of the embodiment of FIG. 3 comprising carbon dioxide treatment 20' rather than wash 20.

Carbon dioxide treatment 20' may comprise contacting the organic stream with water and carbon dioxide, whereby sodium is extracted from the organic stream, and separating an aqueous sodium-containing slurry phase from a pretreated organic phase or stream comprising a reduced sodium content relative to the contaminated organic stream. In embodiments, such carbon dioxide removal of contaminant is performed as described in U.S. Patent Application No. 62/454,542, filed Feb. 3, 2017, the disclosure of which is hereby incorporated herein in its entirety for purposes not contrary to this disclosure.

Without limitation, the carbon dioxide can be combined in an aqueous phase prior to contacting with the organic stream, or the carbon dioxide can be combined with a mixture of the organic stream and water. In embodiments, the carbon dioxide treatment replaces conventional mineral acid treatment. In other embodiments, carbon dioxide treatment is utilized in combination with (e.g., subsequent to) conventional mineral acid treatment.

In embodiments, contacting the contaminated organic stream with water and carbon dioxide comprises combining the carbon dioxide with the water to form a $CO_2$-saturated water stream, and contacting the $CO_2$-saturated water stream with the contaminated organic stream. In embodiments, contacting the contaminated organic stream with water and carbon dioxide comprises combining the contaminated organic stream and the water to form a mixture, and injecting the carbon dioxide as a gas thereinto.

In embodiments, the contacting of the contaminated organic stream with water and carbon dioxide, the separating of the aqueous sodium-containing slurry phase from the pretreated organic phase comprising a reduced sodium content relative to the contaminated organic stream, or both, are repeated to provide a pretreated organic phase or stream having a further reduced sodium content. In embodiments, the organic stream is subjected to ion exchange to provide a pretreated organic stream having a further reduced sodium content. In embodiments, the contaminated organic stream and the water are present during the contacting of the organic stream with water and carbon dioxide at a volumetric ratio in the range of from 1:1 to 20:1, 1:1 to 5:1, or 1:1 to 2:1.

In embodiments, the organic stream is diluted via combination with one or more other organic chemicals, such as, without limitation, those comprising aliphatic or aromatic groups, prior to contact with carbon dioxide. In embodiments, the one or more other organic chemicals comprise ethylbenzene, toluene, cumene, xylene, hexane, heptane, octane, nonane, decane, etc., or a combination thereof. In embodiments, the contaminated organic stream is combined with ethylbenzene prior to contact of the contaminated organic stream with carbon dioxide. In embodiments, the weight ratio between the contaminated organic stream and the one or more other organic chemicals (e.g., ethylbenzene) is in the range of from 1:10 wt/wt ratio to 2:1 wt/wt ratio, from 1:10 wt/wt ratio to 1:1 wt/wt ratio, or from 1:8 wt/wt ratio to 2:1 wt/wt ratio.

In embodiments, contacting the contaminated organic stream with water and carbon dioxide comprises combining the carbon dioxide with water to form a $CO_2$-saturated water stream, and contacting the $CO_2$-saturated water stream with the contaminated organic stream.

In embodiments, the contaminated organic stream and water (or 'aqueous phase') are combined to form a mixture, and carbon dioxide in injected as a gas thereinto. The carbon dioxide can be provided by a gas selected from the group consisting of pure carbon dioxide and/or other gases comprising greater than 50 volume percent carbon dioxide. In embodiments, the gas comprising greater than 50 volume percent carbon dioxide is a flue gas. The flue gas can comprise greater than 70 volume percent carbon dioxide. In embodiments, the carbon dioxide is provided by a gas comprising greater than 80, 85, 90, 95, 96, 97, 98, or 99 volume percent carbon dioxide.

The carbon dioxide gas can be bubbled, sparged, or otherwise introduced into a mixture comprising the contaminated organic phase and water. For example, a mixing device comprising a sparger, through which carbon dioxide gas bubbles can be introduced into a mixture of the organic and aqueous phases, can be utilized.

Following contacting of the organic phase with carbon dioxide as described hereinabove, the resulting mixture is separated into immiscible phases, via a separation unit. Sodium salts are solubilized in the aqueous phase. Specifically, separation provides an aqueous sodium-containing phase and a pretreated organic phase having reduced sodium content relative to the organic stream, wherein the reduced sodium content is below that obtained via water addition or dilution alone. The separation is operated under conditions that provide an immiscible aqueous sodium-containing phase and a pretreated organic phase having reduced sodium content.

The method can further comprise repeating the contacting of the organic phase with carbon dioxide, the separation of the aqueous phase from the organic phase, or both the contacting and the separating steps one or more times to obtain an organic phase having a further reduced sodium content.

In embodiments, the method further comprises subjecting the organic phase to one or more ion exchange 'polishing' steps, as described hereinabove with reference to guard bed 30, to further reduce the sodium content of the organic phase.

Features

The system and method of this disclosure provide for upgrading of an organic stream, such as a by-product formed in the co-production of propylene oxide and styrene. The process of the disclosure comprises subjecting the organic stream to hydrodeoxygenation to convert at least a portion of the oxygenate(s) to EB, and subsequent separation of the EB from the hydrotreatment product containing same. The organic stream can be pretreated for the removal of contaminant therefrom prior to hydrotreatment. Such pretreatment can comprise contacting with carbon dioxide and water, and separating the resulting mixture into an aqueous sodium salt containing phase and a pretreated organic phase having reduced sodium content; acid wash and subsequent neutralization to provide a pretreated organic stream; and/or passage through a guard bed to provide a pretreated organic stream. The disclosed system and method enable production of an upgraded residual stream, which may be utilized for fuel or as a precursor to chemical(s), and EB from a low value PO or POSM by-product stream.

The following examples merely illustrate the system and method of this disclosure. Those skilled in the art will recognize many variations that are within the spirit of this disclosure and the scope of the claims.

EXAMPLES

Example 1

Three (3) kg of a sodium contaminated by-product stream generated during PO and styrene coproduction in a POSM plant was diluted in a 1:1 mass ratio with EB as diluent. The resulting solution was washed with 1.2 kg of 10% sulfuric acid solution by recirculating the mixture with a pump, and the mixture was allowed to settle overnight before separating the aqueous phase. The procedure was repeated with water, 5% $(NH_4)_2CO_3$ solution in water, and again with water, resulting in a neutral pretreated feed. The pretreated feed was then combined with 1.2 kg of additional non-contaminated by-product streams generated during PO and styrene coproduction, and 5.4 kg additional EB, to provide an organic, oxygenate-containing feed containing 2 parts of EB to 1 part of POSM co-products was used as a hydrotreatment feed consisting of a mixture of MBA (3.2 wt % according to GC), ACP (3.0 wt %), PEA, ethers of MBA and PEA (3 wt %), and ring opening products of PO (~1 wt %), along with smaller and GC-invisible components, as well as 12 ppm of sodium.

Example 2

The feed produced in Example 1 combined with 15 ppm dimethyldisulfite was continuously supplied at a rate of 40 mL/h, along with $H_2$ gas at a rate of 170 sccm into a 1 inch fixed bed reactor tube containing 40 g of activated NiMo catalyst KL8234 (available from Criterion Catalysts) having 500 hours on stream before the start of the experiment. The reactor was operated in down flow mode at 1000 psig pressure, maintaining a temperature gradient from 300° C. at the top of the bed to 360° C. at the bottom of the bed via an external clam-shell furnace. A 1471 g portion of the HDO product was separated from water and subjected to EB recovery using a vacuum rotational evaporator (20 mmHg, 80° C.), resulting in 1325 g of EB light fraction with 95% EB content and 133 g light yellow residual material containing ~9 wt % EB, 24 wt % of 2,3-diphenylbutane (~1:1 meso:rac), ~14 wt % other diphenybutane isomers, ~1 wt % phenol. The residual material after EB recovery had low viscosity of 3 cP at 40° C., a density of 0.9224 g/mL, an elemental composition of 89.3 mole % C and 10.6 mole % H, and a caloric value of 18678 Btu/lb.

The preparative EB recovery level calculated based on the EB content of the light fraction was 56 wt % (EB leftover in residual material was not counted).

Example 3

Fifteen (15) kg of pretreated feed batch containing 10 kg of ethylbenzene diluent along with a mixture of various by-product streams generated during PO and styrene coproduction in a POSM plant (sodium contaminated and non-contaminated) were prepared similar to Example 1. The material containing 2 parts of EB to 1 part of POSM co-products was used as a hydrotreatment feed consisting of a mixture of MBA (2.5 wt % according to GC), ACP (<0.1 wt %), PEA (5.2%), ethers of MBA (3 wt %), and ring opening products of PO (~1 wt %), along with smaller and GC-invisible components, as well as 30 ppm of sodium.

Example 4

The feed produced in Example 3 combined with 15 ppm dimethyldisulfite was continuously supplied at a rate of 40 mL/h, along with $H_2$ gas at a rate of 170 sccm, into a 1 inch fixed bed reactor tube containing 40 g of activated NiMo catalyst KL8234 (available from Criterion Catalysts) having 1100 hours on stream before the start of the experiment. The reactor was operated in down flow mode at 1000 psig pressure, maintaining a temperature gradient from 280° C. at the top of the bed to 350° C. at the bottom of the bed via an external clam-shell furnace. A 448 g portion of the HDO product was separated from water and subjected to EB recovery using a vacuum rotational evaporator (20 mmHg, 80° C.), resulting in 380 g of EB light fraction with 97% EB content. and 48 g dark amber residual material containing ~3 wt % EB, 2.8% PEA; 21.5 wt % of 2,3-diphenylbutane (~1:1 meso:rac), ~14 wt % other diphenybutane isomers, ~1.5 wt % phenol. The preparative EB recovery level calculated based on the EB content of the light fraction was 55 wt %.

ADDITIONAL DISCLOSURE

The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and such variations are considered within the scope and spirit of the present disclosure. Alternative embodiments that result from combining, integrating, and/or omitting features of the embodiment(s) are also within the scope of the disclosure. While compositions and methods are described in broader terms of "having", "comprising," "containing," or "including" various components or steps, the compositions and methods can also "consist essentially of" or "consist of" the various components and steps. Use of the term "optionally" with respect to any element of a claim means that the element is required, or alternatively, the element is not required, both alternatives being within the scope of the claim.

Numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an", as used in the claims, are defined herein to mean one or more than one of the element that it introduces. If there is any conflict in the usages of a word or term in this specification and one or more patent or other documents, the definitions that are consistent with this specification should be adopted.

Embodiments disclosed herein include:

A: A method comprising: (a) subjecting an organic stream comprising at least one oxygenate to hydrotreatment, whereby a hydrotreatment product comprising ethylbenzene is produced, wherein the organic stream is a product of a process for the production of propylene oxide; and (b) separating an ethylbenzene product stream from the hydrotreatment product, to yield a residual stream.

B: A method comprising: (a) providing a contaminated organic stream comprising at least one oxygenate and sodium contamination, wherein the organic stream is a product of a process for the production of propylene oxide; (b) reducing the level of sodium in the contaminated organic stream, to provide a pretreated organic stream; (c) subjecting the pretreated organic stream to hydrotreatment, whereby a hydrotreatment product comprising ethylbenzene is produced; and (d) separating an ethylbenzene product stream from the hydrotreatment product, to provide a residual stream.

C: A method comprising: (a) subjecting an organic stream comprising at least one oxygenate to hydrotreatment, whereby a hydrotreatment product comprising ethylbenzene is produced, wherein the organic stream is a product of a process for the co-production of propylene oxide and styrene monomer (POSM); and (b) separating an ethylbenzene product stream from the hydrotreatment product, to yield a residual stream.

Each of embodiments A, B, and C may have one or more of the following additional elements:

Element 1: wherein the hydrotreatment is carried out in the presence of a hydrotreatment catalyst comprising molybdenum. Element 2: wherein the hydrotreatment catalyst further comprises nickel, cobalt, or a combination thereof. Element 3: wherein the hydrotreatment catalyst is a sulfided catalyst. Element 4: wherein the hydrotreatment catalyst comprises NiMo, CoMo, or a combination thereof. Element 5: wherein the catalyst exhibits low selectivity to one or more byproducts. Element 6: wherein the hydrotreatment product comprises less than or equal to 0.2, 0.5, 1, or 3 weight percent selectivity to ethylcyclohexane byproduct. Element 7: wherein the organic stream is a product of a process for the co-production of propylene oxide and styrene monomer (POSM). Element 8: wherein the hydrotreatment is carried out in the presence of a diluent. Element 9: wherein the diluent comprises ethylbenzene. Element 10: wherein the organic stream is combined with the diluent at a mass ratio in the range of from 1:0.1 to 1:10, from 1:0.5 to 1:5, from 1:1 to 1:3, or equal to 1:1.5, 1:2, or 1:2.5. Element 11: wherein the ethylbenzene recovery, defined as the weight percent of the POSM organic stream before hydrotreatment that is converted to ethylbenzene, is greater than 20, 30, 40, 50 or 60 wt %. Element 12: wherein the organic stream comprises a contaminant selected from sodium, potassium, or both, and wherein the method further comprises removing at least a portion of the contaminant to provide a pretreated organic stream, prior to subjecting the pretreated organic stream to hydrotreatment. Element 13: wherein the contaminant comprises sodium. Element 14: wherein the organic stream comprises greater than or equal to 100, 1000, 5000, or 10000 ppm sodium, and wherein the pretreated organic stream comprises less than 100, 10, or 1 ppm sodium. Element 15: wherein the organic stream is a product of a process for the co-production of propylene oxide and styrene (POSM), and wherein removing at least a portion of the contaminant prior to hydrotreatment comprises: (c) contacting the organic stream with water and carbon dioxide, whereby sodium is extracted from the organic stream; and separating an aqueous sodium-containing slurry phase from a pretreated organic phase comprising a reduced sodium content relative to the organic stream; (d) subjecting the organic stream to an acid wash and subsequent neutralization to provide the pretreated organic stream; (e) passing the organic stream over a catalyst guard bed to provide a pretreated stream prior to hydrotreatment; or a combination thereof. Element 16: wherein (d) subjecting the organic stream to acid wash comprises contacting the organic stream with sulfuric acid, to provide an acid washed organic stream. Element 17: wherein neutralization comprises contacting the acid washed organic stream with a carbonate, with crushed marble, or a combination thereof. Element 18: wherein the carbonate comprises ammonium carbonate, sodium carbonate, or both. Element 19: further comprising washing with water subsequent to acid wash, neutralization, or both. Element 20: wherein the contacting in (c) comprises combining the carbon dioxide with the water to form a $CO_2$-saturated water stream, and contacting the $CO_2$-saturated water stream with the organic stream. Element 21: wherein the contacting in (c) comprises combining the organic stream and the water to form a mixture, and injecting the carbon dioxide as a gas thereinto. Element 22: further comprising: repeating the contacting, the separating, or both the contacting and the separating of (c) one or more times on the organic phase; subjecting the organic phase to ion exchange; or both, to obtain a pretreated organic phase having a further reduced sodium content. Element 23: wherein the organic stream and the water are present in (c) at a volumetric ratio in the range of from 1:1 to 20:1, 1:1 to 5:1, or 1:1 to 2:1. Element 24: further comprising subjecting at least a portion of the hydrotreatment product to further hydrotreatment. Element 25: wherein (b) separating the ethylbenzene product stream from the hydrotreatment product comprises distillation. Element 26: wherein distillation comprises subjecting the hydrotreatment product to a first distillation to separate the hydrotreatment product into a light stream comprising primarily ethylbenzene, and a heavy stream comprising the residual stream; subjecting the light stream, the heavy stream, or both to further distillation to provide one or more further distilled streams; recycling the light stream, the heavy stream, a further distilled stream, or a combination thereof to the hydrotreatment; or a combination thereof. Element 27: further comprising recycling at least a portion of the ethylbenzene product stream, at least a portion of the residual stream, or both, to the hydrotreatment in (a). Element 28: wherein separating the ethylbenzene product stream from the hydrotreatment product comprises recovering at least 20, 30, 40, or 50 weight percent of the ethylbenzene from the hydrotreatment product, and wherein the residual stream comprises greater than or equal to 5, 10, 20, 50, or 70 weight percent diphenylbutane isomers. Element 29: wherein the residual stream comprises diphenylbutane isomers. Element 30: wherein the residual stream comprises primarily diphenylbutane isomers. Element 31: wherein the residual stream comprises greater than or equal to 5, 10, 20, or 30 weight percent 2,3-diphenylbutane. Element 32: further comprising crystallizing the meso form of the 2,3-diphenylbutane, and separating it from the residual stream. Element 33: wherein the residual stream has a higher fuel value than the organic stream. Element 34: wherein the residual stream has a higher caloric value than the organic stream. Element 35: wherein the residual stream has a density that is at least 3, 5, or 10 percent less than the density of the organic stream, wherein the residual stream comprises an oxygen content that is 20-100, or at least 70, 90, or 100 percent less than the oxygen content of the organic stream, wherein the residual stream has a viscosity of less than or equal to 20 cP, 10 cP, or 5 cP at 40° C., or a combination thereof. Element 36: wherein the residual stream has a density of less than or equal to 0.97, 0.95, or 0.91 g/mL, wherein the residual stream has an oxygen content of less than or equal to 5, 2, or 0 wt %, wherein the residual stream has a viscosity of less than or equal to 10 cP at 40° C., or a combination thereof. Element 37: wherein the at least one oxygenate is selected from methylbenzyl alcohol (MBA), 2-phenyl ethanol (PEA), ethers, acetophenone (ACP), ethers of MBA and PEA, propylene oxide ring opening compounds, oligomers, or a combination thereof. Element 38: wherein the organic stream is a POSM by-product stream that has not been treated to remove heavies therefrom. Element 39: wherein the organic stream is an ACP/MBA stream from a POSM process. Element 40: wherein the conversion of the at least one oxygenate to ethylbenzene is greater than or equal to 90, 93, or 95%. Element 41: wherein (a) subjecting the organic stream comprising at least one oxygenate to hydrotreatment comprises introducing the organic stream to more than one hydrotreatment reactor in series, introducing the organic stream to more than one hydrotreatment reactor in parallel, operating the hydrotreatment at a reduced extent of reaction and recycling the hydrotreatment product to the hydrotreatment, or a combination thereof. Element 42: wherein the hydrotreatment is carried out at an inlet temperature in the range of from 150-300° C., from 180-280° C., or from 200-250° C.; an outlet temperature of greater than or equal to 300° C., 350° C., or 400° C.; a pressure in the range of from 300-2000 psig, from 500-1500 psig, or from 800-1200 psig; a liquid hourly space velocity (LHSV) in the range of from 0.1-10, from 0.5-5, or from 0.8-2; or a combination thereof. Element 43: wherein the hydrotreatment is continuous. Element 44: further comprising controlling the exothermicity of the hydrotreatment by operating the hydrotreatment at a reduced extent of reaction and recycling the hydrotreatment product to the hydrotreatment, adjusting the amount of a diluent combined with the organic stream, operating a plurality of hydrotreatment reactors in series, or a combination thereof. Element 45: wherein reducing the level of sodium in the contaminated organic stream to provide the pretreated organic stream comprises: contacting the contaminated organic stream with water and carbon dioxide, whereby sodium is extracted from the contaminated organic stream; and separating an aqueous sodium-containing phase from an organic phase comprising a reduced sodium content relative to the contaminated organic stream; subjecting the contaminated organic stream to an acid wash and subsequent neutralization to provide the pretreated organic stream; passing the contaminated organic stream over a catalyst guard bed prior to h hydrotreatment; or a combination thereof. Element 46: further comprising: reusing the separated ethylbenzene product as a feed in the process for the co-production of propylene oxide and styrene monomer.

While certain embodiments have been shown and described, modifications thereof can be made by one skilled in the art without departing from the teachings of this disclosure.

Numerous other modifications, equivalents, and alternatives, will become apparent to those skilled in the art once the above disclosure is fully appreciated. It is intended that the following claims be interpreted to embrace such modifications, equivalents, and alternatives where applicable. Accordingly, the scope of protection is not limited by the description set out above but is only limited by the claims which follow, that scope including equivalents of the subject matter of the claims.

What is claimed is:

1. A method comprising:
   (a) Subjecting ethylbenzene and oxygen to a propylene oxide (PO) production process or a propylene oxide and styrene monomer (POSM) co-production process to produce an effluent;
   (b) Separating ethylbenzene and styrene from the effluent and recovering an organic stream comprising at least one oxygenate;
   (c) Subjecting the organic stream to a hydrotreatment in the presence of a hydrotreatment catalyst comprising molybdenum, to produce a hydrotreatment product comprising ethylbenzene; and,
   (d) Separating an ethylbenzene product stream from the hydrotreatment product, to yield a residual stream.

2. The method of claim 1, wherein the hydrotreatment catalyst further comprises nickel, cobalt, or a combination thereof.

3. The method of claim 2, wherein the hydrotreatment catalyst is a sulfided catalyst.

4. The method of claim 1, further comprising recycling the ethylbenzene product stream to the PO/POSM process.

5. The method of claim 1, wherein the hydrotreatment is carried out in the presence of a diluent, wherein the diluent comprises ethylbenzene, recycled ethylbenzene, or a portion of a bottoms from a distillation tower.

6. The method of claim 1, wherein the ethylbenzene recovery, defined as the weight percent of the organic stream before hydrotreatment that is converted to ethylbenzene, is greater than 20 wt %.

7. The method of claim 1, wherein the organic stream comprises a contaminant selected from sodium, potassium, or both, and wherein the method further comprises removing at least a portion of the contaminant to provide a pretreated organic stream, prior to subjecting the pretreated organic stream to hydrotreatment.

8. The method of claim 7, wherein removing at least a portion of the contaminant prior to hydrotreatment comprises:
   (e) contacting the organic stream with water and carbon dioxide, whereby sodium is extracted from the organic stream, and separating an aqueous sodium-containing slurry phase from an organic phase comprising a reduced sodium content relative to the organic stream; passing the organic stream over a catalyst guard bed prior to hydrotreatment; or both contacting the organic stream with water and carbon dioxide, whereby sodium is extracted from the organic stream, and separating an aqueous sodium-containing slurry phase from an organic phase comprising a reduced sodium content relative to the organic stream; and passing the organic stream over a catalyst guard bed prior to hydrotreatment; or (f) subjecting the organic stream to an acid wash and subsequent neutralization to provide the pretreated organic stream; passing the organic stream over a catalyst guard bed prior to hydrotreatment; or both subjecting the organic stream to an acid wash and subsequent neutralization to provide the pretreated organic stream and passing the organic stream over a catalyst guard bed prior to hydrotreatment.

9. The method of claim 8, wherein the contacting in (e) comprises combining the carbon dioxide with the water to form a $CO_2$-saturated water stream, and contacting the $CO_2$-saturated water stream with the organic stream; combining the organic stream and the water to form a mixture, and injecting the carbon dioxide as a gas thereinto; or both.

10. The method of claim 1 further comprising subjecting at least a portion of the hydrotreatment product to further hydrotreatment.

11. The method of claim 1, wherein (d) separating the ethylbenzene product stream from the hydrotreatment product comprises distillation.

12. The method of claim 1 further comprising recycling at least a portion of the ethylbenzene product stream, at least a portion of the residual stream, or both, to the hydrotreatment in (c).

13. The method of claim 1, wherein the residual stream comprises diphenylbutane isomers.

14. The method of claim 1, wherein the at least one oxygenate is selected from methylbenzyl alcohol (MBA), 2-phenyl ethanol (PEA), ethers, acetophenone (ACP), ethers of MBA and PEA, propylene oxide ring opening compounds, or a combination thereof.

15. A method comprising:
(a) Subjecting ethylbenzene and oxygen to a propylene oxide (PO) production process or a propylene oxide and styrene monomer (POSM) co-production process to produce an effluent;
(b) Separating ethylbenzene and styrene from the effluent and recovering an organic stream comprising at least one oxygenate and sodium contamination;
(c) Reducing the level of sodium in the contaminated organic stream, to provide a pretreated organic stream;
(d) Subjecting the pretreated organic stream to a hydrotreatment in the presence of a hydrotreatment catalyst comprising molybdenum to produce a hydrotreatment product comprising ethylbenzene;
(e) Separating an ethylbenzene product stream from the hydrotreatment product, to provide a residual stream.

16. The method of claim 15, wherein reducing the level of sodium in the contaminated organic stream to provide the pretreated organic stream comprises:
(f) contacting the contaminated organic stream with water and carbon dioxide, whereby sodium is extracted from the contaminated organic stream, and separating an aqueous sodium-containing phase from an organic phase comprising a reduced sodium content relative to the contaminated organic stream; passing the contaminated organic stream over a catalyst guard bed prior to hydrotreatment; or both contacting the contaminated organic stream with water and carbon dioxide, whereby sodium is extracted from the contaminated organic stream, and separating an aqueous sodium-containing phase from an organic phase comprising a reduced sodium content relative to the contaminated organic stream; and passing the contaminated organic stream over a catalyst guard bed prior to hydrotreatment; or
(g) subjecting the contaminated organic stream to an acid wash and subsequent neutralization to provide the pretreated organic stream; passing the contaminated organic stream over a catalyst guard bed prior to hydrotreatment; or both subjecting the contaminated organic stream to an acid wash and subsequent neutralization to provide the pretreated organic stream; and passing the contaminated organic stream over a catalyst guard bed prior to hydrotreatment.

17. A method comprising:
(a) Subjecting ethylbenzene and oxygen to a propylene oxide (PO) production process or a propylene oxide and styrene monomer (POSM) co-production process to produce an effluent;
(b) Separating ethylbenzene and styrene from the effluent and recovering an organic stream comprising at least one oxygenate;
(c) Subjecting the organic stream to a hydrotreatment in the presence of a hydrotreatment catalyst comprising molybdenum to produce a hydrotreatment product comprising ethylbenzene;
(d) Separating an ethylbenzene product stream from the hydrotreatment product, to yield a residual stream; and
(e) Reusing the separated ethylbenzene product as a feed in the process for the coproduction of propylene oxide and styrene monomer propylene oxide (PO) production process or the propylene oxide and styrene monomer (POSM) co-production process.

18. The method of claim 17, wherein the organic stream comprises a contaminant selected from sodium, potassium, or both, and wherein the method further comprises removing at least a portion of the contaminant to provide a pretreated organic stream, prior to subjecting the pretreated organic stream to hydrotreatment.

19. The method of claim 15, further comprising the step of recycling the ethylbenzene product stream to the PO/POSM process.

* * * * *

UNITED STATES PATENT AND TRADEMARK OFFICE
CERTIFICATE OF CORRECTION

PATENT NO. : 10,526,549 B2  
APPLICATION NO. : 15/961651  
DATED : January 7, 2020  
INVENTOR(S) : Sandor Nagy et al.

Page 1 of 1

It is certified that error appears in the above-identified patent and that said Letters Patent is hereby corrected as shown below:

On the Title Page
| | | |
|---|---|---|
| Item (71) | Line 1 | After "Technology,", insert --L.P.,-- |
| Item (56) Other Publications | Line 5 | Delete "Iwak et al.," and insert --Kwak et al.,-- |

In the Specification
| | | |
|---|---|---|
| Column 4 | Line 25 | Delete "bout" and insert --about-- |
| Column 6 | Line 23 | After "stream", delete "line" |
| Column 6 | Line 34 | After "stream", delete "line" |
| Column 11 | Line 20 | Delete "2603." and insert --260B'.-- |
| Column 16 | Line 45 | Delete "content." and insert --content,-- |
| Column 20 | Line 8 | After "to", delete "h" |

In the Claims
| | | |
|---|---|---|
| Column 20 | Line 38 | In Claim 1, delete "and," and insert --and-- |
| Column 22 | Line 45 | In Claim 17, after "in the", delete "process for the coproduction of propylene oxide and styrene monomer" |

Signed and Sealed this  
Thirty-first Day of March, 2020

Andrei Iancu  
*Director of the United States Patent and Trademark Office*